US012788901B2

(12) United States Patent
Allerdings

(10) Patent No.: US 12,788,901 B2
(45) Date of Patent: Nov. 10, 2026

(54) TOUCH SENSOR OF A DRUG DELIVERY DEVICE OR OF A DRUG DELIVERY ADD-ON DEVICE

(71) Applicant: Sanofi, Paris (FR)

(72) Inventor: Alexander Allerdings, Frankfurt am Main (DE)

(73) Assignee: SANOFI, Paris (FR)

( * ) Notice: Subject to any disclaimer, the term of this patent is extended or adjusted under 35 U.S.C. 154(b) by 596 days.

(21) Appl. No.: 18/034,797

(22) PCT Filed: Nov. 9, 2021

(86) PCT No.: PCT/EP2021/081062
§ 371 (c)(1),
(2) Date: May 1, 2023

(87) PCT Pub. No.: WO2022/101179
PCT Pub. Date: May 19, 2022

(65) Prior Publication Data
US 2023/0405241 A1 Dec. 21, 2023

(30) Foreign Application Priority Data
Nov. 10, 2020 (EP) .................................... 20315448

(51) Int. Cl.
*A61M 5/148* (2006.01)
*A61M 5/48* (2006.01)

(52) U.S. Cl.
CPC ..... *A61M 5/486* (2013.01); *A61M 2205/3331* (2013.01)

(58) Field of Classification Search
CPC ............ A61M 2205/582; G16H 20/17; H01H 2003/0293
See application file for complete search history.

(56) References Cited

U.S. PATENT DOCUMENTS 8,556,867 B2 * 10/2013 Krulevitch .............. A61M 5/24
604/246
10,431,068 B2 * 10/2019 Sala Cunill ............. A61M 5/20
(Continued)

FOREIGN PATENT DOCUMENTS

CN 106020559 A 10/2016
CN 106030467 A 10/2016
(Continued)

OTHER PUBLICATIONS

Notice of Reasons for Refusal, JP Patent Application No. 2023-527675, dated Feb. 18, 2025, pp. 1-8 (with pp. 1-4 being a translation).
(Continued)

*Primary Examiner* — Laura A Bouchelle
(74) *Attorney, Agent, or Firm* — Bond, Schoeneck & King, PLLC

(57) ABSTRACT

A touch sensor of a drug delivery device or of a drug delivery add-on device including a rigid element, a touch element arranged in relation to the rigid element such that a gap between at least a part of the rigid element and a flexible part of the touch element is provided, at least one pressure sensitive element arranged between the rigid element and the flexible part of the touch element in the gap such that a pressure applied to the flexible part of the touch element deforms the flexible part to reduce the gap and transmit the applied pressure to the pressure sensitive element, wherein the at least one pressure sensitive element is configured to generate an output signal upon detecting the pressure applied to the pressure sensitive element, the generated output signal being provided for signaling that the flexible part of the touch element has been touched.

18 Claims, 5 Drawing Sheets

(56) References Cited

U.S. PATENT DOCUMENTS

| | | | | |
|---|---|---|---|---|
| 2003/0058223 | A1 | 3/2003 | Tracy et al. | |
| 2012/0038583 | A1 | 2/2012 | Westhues et al. | |
| 2012/0212434 | A1 | 8/2012 | Bluemler et al. | |
| 2014/0005950 | A1 * | 1/2014 | Groeschke ............. | G16H 40/40<br>702/19 |
| 2019/0269859 | A1 | 9/2019 | Jacobsen | |

FOREIGN PATENT DOCUMENTS

| | | | |
|---|---|---|---|
| CN | 106581822 | | 4/2017 |
| CN | 106581822 | A | 4/2017 |
| CN | 108140360 | A | 6/2018 |
| CN | 111741784 | A | 10/2020 |
| EP | 2296728 | | 10/2019 |
| JP | 2014512879 | A | 5/2014 |
| JP | 2014516599 | A | 7/2014 |
| WO | WO 2018/044425 | | 3/2018 |
| WO | WO 2022/101179 | | 5/2022 |

OTHER PUBLICATIONS

International Search Report and Written Opinion in International Appln. No. PCT/EP2021/081062, mailed on Dec. 8, 2021, 10 pages.
First Office Action for Chinese Patent Application No. 202180074966.8 dated Nov. 26, 2025 and Search Report dated Nov. 24, 2025 (13 pages, of which 6 are English).
Supplementary Search for Chinese Patent Application No. 202180074966.8, dated May 13, 2026 (1 page).

* cited by examiner

TOUCH SENSOR OF A DRUG DELIVERY DEVICE OR OF A DRUG DELIVERY ADD-ON DEVICE

CROSS-REFERENCE TO RELATED APPLICATIONS

The present application is the national stage entry of International Patent Application No. PCT/EP2021/081062, filed on Nov. 9, 2021, and claims priority to Application No. EP 20315448.9, filed on Nov. 10, 2020, the disclosures of which are incorporated herein by reference.

TECHNICAL FIELD

The present disclosure relates to a touch sensor of a drug delivery device or of a drug delivery add-on device.

BACKGROUND

EP2296728B1 relates to an administration device for supplying an injectable or infusible product into an organism, in particular a patient, in particular to an infusion device for therapeutic applications, for example a portable infusion device, which can be adapted for self-administering medicines such as insulin over an extended period of time. A device disclosed in EP2296728B1 is characterized by a touch sensor for generating an activation signal, wherein the touch sensor is incorporated into a button or is located in the vicinity of a button, such as in an area neighboring and/or partly or fully surrounding the button. For a touch sensor which is arranged in this way, the activation signal is generated if a patient's finger physically touches the button or is close enough to the button such that it can be assumed that the patient intends to operate the button. That is, the same movement of the patient's finger may first cause the touch sensor to generate the activation signal, followed by pressing the button.

US2014005950A1 relates to an apparatus and a method for detecting an actuation action that is performable with a medical device to cause the medical device to eject a medicament that is comprised in the medical device. The apparatus comprises a detector unit comprising a detector configured to detect an actuation action performable via the detector unit to an actuation button of a medical device to cause the medical device to eject at least a portion of a medicament comprised in the medical device. Therein, the detector is configured to detect the actuation action based on a detection of a force and/or a touch applied to the detector unit as part of the actuation action. The apparatus further comprises an electric unit connected to the detector and configured to store and/or provide information related to the detected actuation action.

US2019269859A1 relates generally to devices for delivering medicine to a subject, and more specifically to injection devices capable of setting and expelling one or more doses of drug from a drug reservoir. A drug injection device comprises a housing having a deflectable exterior housing surface portion capable of deflection relative to other exterior housing surface portions, and an activation element configured to undergo movement relative to the housing corresponding to an action performed on or by the injection device and to actuate, i.e. deflect, the deflectable exterior housing surface portion during said movement.

US2012212434A1 relates to a technical medical device, in particular a blood treatment device having at least one touchscreen and a method for display and input of information in a blood treatment device having at least one touchscreen. US2012212434A1 discloses a technical medical device, in particular a dialysis machine, having at least one touchscreen, whereby the touchscreen has two redundant sensors for detecting the position of a finger pressing on the touchscreen.

SUMMARY

This disclosure describes a touch sensor of a drug delivery device or of a drug delivery add-on device, which may be particularly used for generating a wake-up signal for electronics of a drug delivery device or of a drug delivery add-on device, for example electronics configured for detecting a selected and/or expelled medicament dosage. The electronics may be for example implemented as an electronic coding module for application in a drug delivery device or an add-on device for a drug delivery device and configured for detecting, storing and/or transmitting selected and/or expelled medicament dosages.

In one aspect the present disclosure describes a touch sensor of a drug delivery device or of a drug delivery add-on device, wherein the touch sensor comprises a rigid element, a touch element arranged in relation to the rigid element such that a gap between at least a part of the rigid element and a flexible part of the touch element is provided, at least one pressure sensitive element arranged between the rigid element and the flexible part of the touch element in the gap such that a pressure exercised on the flexible part of the touch element deforms the flexible part, and the deformation at least partly reduces the gap and at least partly transmits the exercised pressure to the pressure sensitive element, wherein the at least one pressure sensitive element is configured to generate an output signal upon exercising a pressure on the pressure sensitive element, the generated output signal being provided for signaling a touch of the flexible part of the touch element. The touch sensor may be used for example to generate a signal for waking up an electronics of a drug delivery device or a drug delivery add-on device, particularly an electronics for detection and recording of a medicament dosage selected and delivered with the drug delivery device. Particularly, the touch sensor may be integrated in a dial grip of a drug delivery device or a drug delivery add-on device to detected a touch of the dial grip and generate a corresponding signal, which can then be used to wake-up an electronics configured for detecting particularly the selecting of a medicament dosage by turning the dial grip.

In an embodiment, the rigid element may comprise at least in part a cylindrical shape and the touch element is shaped as a sleeve coaxially arranged to the cylindrically shaped part of the rigid element. This embodiment may be particularly applicable for pen shaped drug delivery devices, such as drug injection pens, with cylindrically shaped bodies which are touched by patients like pens when using them.

In a further embodiment, the rigid element and the touch element both may form at least a part of the housing of the drug delivery device or the drug delivery add-on device. For example, the sleeve may form an outer and partly flexible shell, particularly made from a flexible plastic material, of a dial grip provided for selecting a medicament dosage, while the rigid element may be formed by an inner part of the drug delivery device or drug delivery add-on device such as a body housing a mechanism for drug delivery.

In a yet further embodiment, the at least one pressure sensitive element may comprise a vibration element configured for generating vibrations of the touch element and for changing the generated vibrations upon exercising a pressure on the pressure sensitive element. Particularly, the at least one pressure sensitive element may comprise one of a piezoelectric actuator, an electromechanical element, particularly a vibration motor. The vibration element may be an active element, which means that it is excited by applying an electric voltage and current to produce vibrations. In a still further embodiment, the touch sensor may comprise a vibration controller configured for controlling the vibration element to generate continuous and/or impulse vibrations of the touch element and for generating the output signal depending on detecting a changing of the generated vibrations. Particularly, the vibration controller may be configured to control sensitivity and/or power demand of the at least one pressure sensitive element by setting duration and/or pulsing of the impulse vibrations, and/or amplitude and/or frequency of the continuous vibrations. For example, by setting the duration and/or pulsing or the amplitude and/or frequency, the sensitivity may be optimized, particularly increased to a maximum at a given power demand. More particularly, the vibration controller may be configured to set the frequency of the continuous vibrations in a range comprising a resonance frequency of the drug delivery device or the drug delivery add-on device. With this setting, a particular energy efficiency may be achieved.

In embodiments, the at least one pressure sensitive element may comprise a piezoelectric sensor. The piezoelectric sensor may be configured as an active element for generating an electric signal as the output signal upon exercising a pressure on it. The piezoelectric element may be configured as a passive element changing a parameter upon exercising a pressure on it, such as a piezoelectric capacitor, which measurably changes its capacitance upon exercising pressure.

In embodiments, the touch sensor may comprise a processor configured for processing the output signal of the at least one pressure sensitive elements by detecting a change of a parameter of the output signal. The parameter may be for example the amplitude, frequency, clock, duration of the output signal. The processor may allow to directly produce one or more signals for an electronics of a drug delivery device or drug delivery add-on device, such as for example a digital wake-up signal. The processor may be for example implemented by microcontroller, which can be integrated in the touch sensor, which may be configured to control the at least one pressure sensitive element and to generate one or more signals from the output signal generated by the at least one pressure sensitive element. Particularly, the touch sensor may comprise several pressure sensitive elements, and the processor may be configured for generating a differential signal from two or more output signals of the several pressure sensitive elements as the output signal to be processed for detecting a change of the parameter. More particularly, the processor may be configured for outputting a touch detection signal upon detection of a change of the amplitude and/or frequency of the output signal. The touch detection signal may be for example a digital signal, which is set to binary "1" upon detection of a change of the amplitude and/or frequency, and to binary "0" when no change is detected, or vice-versa. Further information may be encoded in the touch detection signal such as for example the magnitude of a detected change.

In embodiments, the touch sensor may comprise an interface for transmitting the output signal, wherein the interface comprise one or more of the following: a wireless interface, particularly a Bluetooth®, Wi-Fi™, ZigBee™, a near filed communication interface; a wired interface, particularly a serial communication bus interface such as 12C, USB. The interface may be used to transmit the output signal for example to an electronics for initiating a recording of a usage of the drug delivery device, particularly for recording the selection of a drug dosage by touching the touch sensor and using a selector at the drug delivery device or drug delivery add-on device to select a drug dosage. Particularly, the receipt of the output signal may be interpreted by an electronics of a drug delivery device or a drug delivery add-on device as wake-up signal for starting a program for detecting a selecting of a drug dosage by a patient.

In a further aspect the present disclosure describes a drug delivery device or a drug delivery add-on device comprising a touch sensor as disclosed herein. The drug delivery device may particularly be a drug injection pen or an add-on for a drug injection pen.

In embodiments, the drug delivery device or a drug delivery add-on device may comprise an electronics configured for one of the following: processing an output signal generated by the at least one pressure sensitive element for determining an user input; transmitting an output signal generated by the at least one pressure sensitive element for determining an user input via an interface; storing an user input determined by processing an output signal generated by the at least one pressure sensitive element.

DETAILED DESCRIPTION

In the following, embodiments of the present disclosure will be described with reference to injection devices, particularly an injection device in the form of a pen. The present disclosure is however not limited to such application and may equally well be deployed with other types of drug delivery devices, particularly with another shape than a pen.

Figure 1:
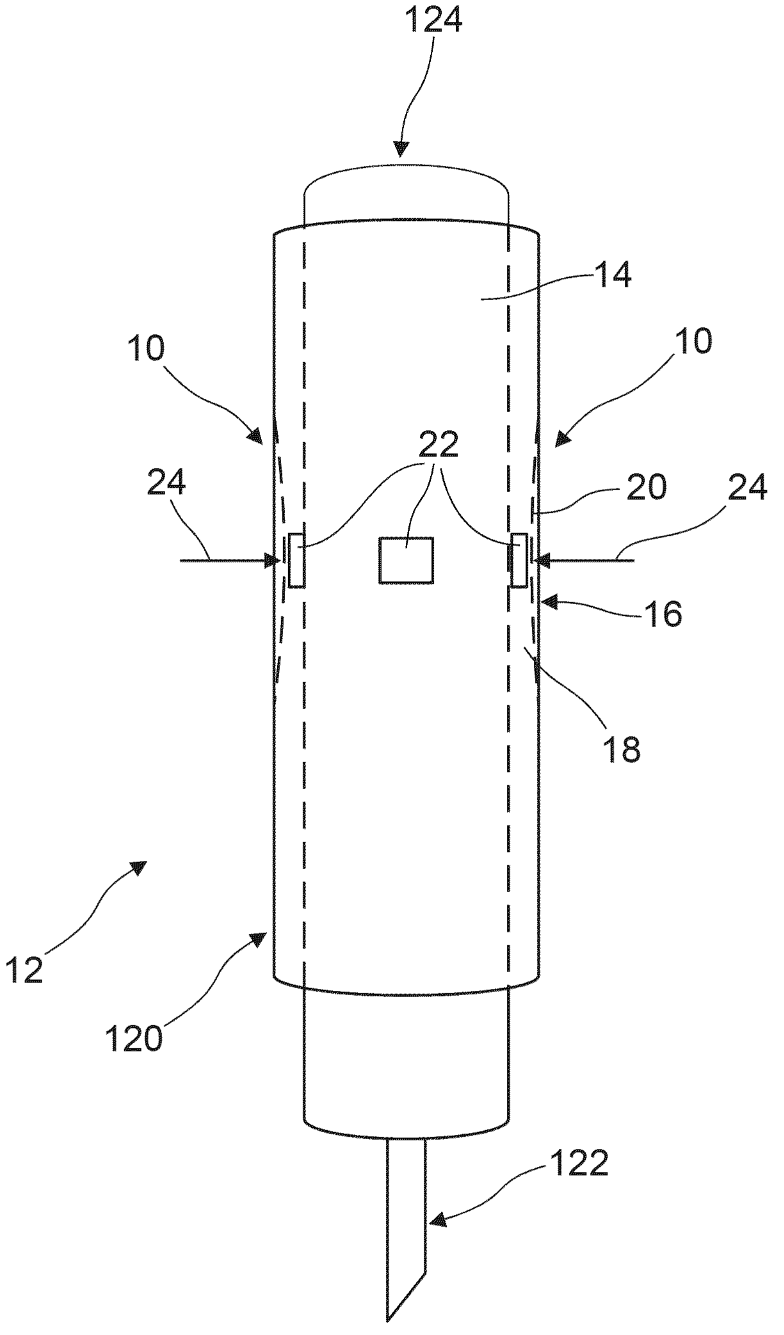
FIG. 1 shows an example of a drug delivery device comprising a touch sensor.

FIG. 1 shows an injection device in the form of an injection pen 12 having a cylindrically shaped body 120. The body 120 is provided for holding a drug cartridge (not shown) and for housing a dosage selecting and expelling mechanism (not shown) and electronics (not shown) for detecting a selection of a drug dosage to be expelled and for recording of the expelled drug dosage. The body 120 has a proximal end and a distal end. A syringe 122 is provided at the proximal end of the body 120 for expelling a selected drug dosage and injecting it into a patient's body, and an injection button 124 is attached to the distal end of the body 120. The injection button 124 may be coupled to the selecting and expelling mechanism such that pressure exerted on the injection button 124 in the longitudinal direction of the body 120 causes the mechanism to expel the selected drug dosage via the syringe 122.

The body 120 may be formed of several elements or parts, and particularly comprises a rigid element 14, which may form a housing for the drug cartridge and the dose selecting and expelling mechanism. A sleeve like shaped touch element 16 may be coaxially arranged to the rigid element 14 such that a gap 18 is provided at least partly between the rigid element 14 and the touch element 16. The touch element 16 is provided to enable a patient to hold the injection pen 12, and particularly to select a drug dosage to be expelled by pressing the injection button 124 via the (not shown) dosage selecting and expelling mechanism internally arranged in the rigid element 14. For the drug dosage selection, the patient may touch the touch element and turn it around the longitudinal axis of the body 120. The rotation of the touch element 16 may cause the dosage selecting mechanism to select a desired drug dosage to be expelled upon pressing the injection button 124.

The touch element 16 is part of a touch sensor 10 of the injection pen 12, as well as the rigid element 14 of the body 120. The touch sensor 10 further comprises several pressure sensitive elements 22 circumferentially arranged in the gap 18 formed between the touch element 16 and the rigid element 14. The pressure sensitive elements 22 may comprise vibration elements, such as piezoelectric actuators, or electromechanical elements like vibration motors, and/or piezoelectric sensors.

The pressure sensitive elements 22 are positioned below a flexible part 20 of the touch element 16 in the gap 18, and may be fixed at the exterior side of the rigid element 14, the interior side of the touch element 16, or both. The pressure sensitive elements 22 may be particularly arranged in the gap to be clamped between the rigid element 14 and the touch element 16, while without any pressure on the touch element 14 the elements 22 do not produce an output signal for indicating a touch of the touch element 16, which means that any output signal of the elements 22 generated without pressure would not mean to indicate a touch. For example, a strain on the pressure sensitive elements 22 due to fabrication tolerances could incur the generation of any signal output of the pressure sensitive elements, but would not be deemed to be an output signal in the sense of the present disclosure.

The flexible part 20 may be for example formed by a thin wall of the touch element or a flexible material. The flexible part 20 is designed to be at least partly deformed upon exercising a pressure on it, particularly when a patient touches the touch element 16 and exercises a pressure 24 on the flexible part, which deforms the later at least partly, as shown in FIG. 1 by the dented part in dotted lines of the touch element 16. The at least partly deformation of the flexible part 20 reduces the gap 18 between the touch element 16 and the rigid element 14 at least in the area below the flexible part 20. This deformation of the flexible part 20 and particularly the reduction of the gap 18 may incur an at least partly transmission of the exercised pressure 24 to one or more of the pressure sensitive elements 22. Even if FIG. 1 shows the pressure 24 as being directed on the area of the flexible part 20 of the touch element 16, under which the pressure sensitive elements 22 are positioned, also a touch at different locations of the touch element 16 may be detectable, when this incurs a deformation of the flexible part 20 so that at least a part of the pressure 24 from the touch can be transmitted to the pressure sensitive elements 22.

Figure 2:
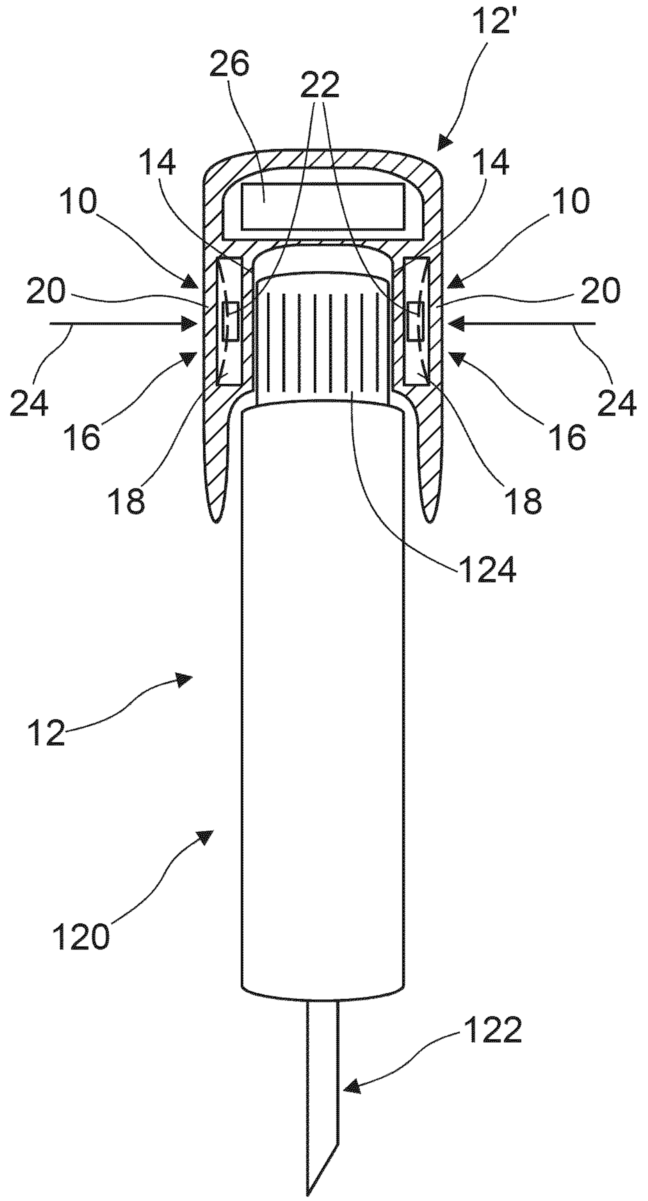
FIG. 2 shows an example of a drug delivery add-on device comprising a touch sensor.

FIG. 2 shows an injection device in the form of an injection pen 12 with an attached add-on device 12'. The injection pen 12 has a cylindrically shaped body 120. The body 120 is provided for holding a drug cartridge (not shown) and for housing a dosage selecting and expelling mechanism (not shown). The body 120 has a proximal end and a distal end. A syringe 122 is provided at the proximal end of the body 120 for expelling a selected drug dosage and injecting it into a patient's body, and an injection button 124 is attached to the distal end of the body 120.

The injection button 124 may be coupled to the selecting and expelling mechanism such that by rotating the injection button 124 around the longitudinal axis of the injection pen 12 a drug dosage to be expelled may be selected, and thereafter a pressure exerted on the injection button 124 in the longitudinal direction of the body 120 may cause the mechanism to expel the selected drug dosage via the syringe 122.

Figure 5:
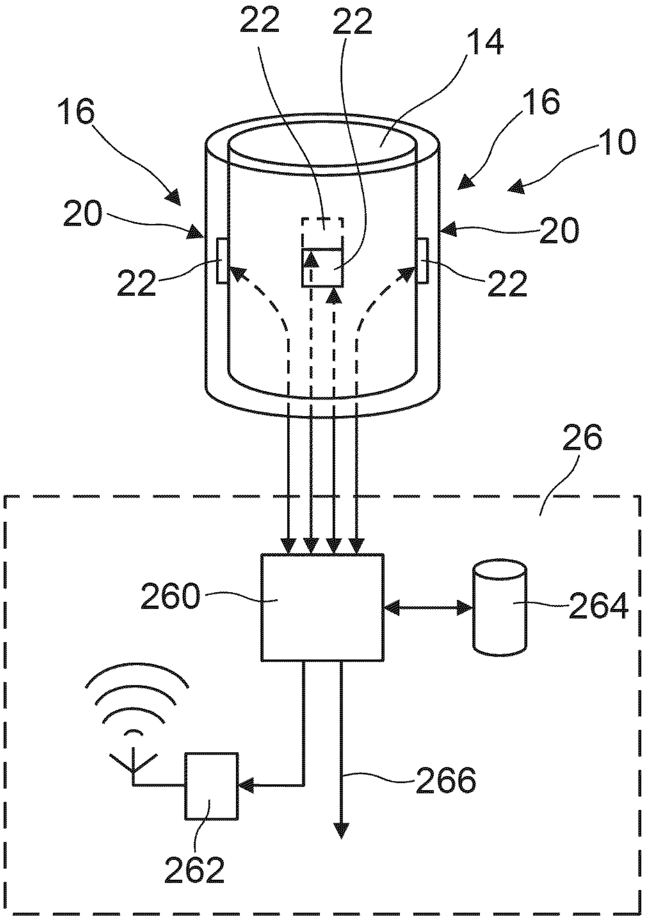
FIG. 5 shows a block diagram of electronic components for a touch sensor.

The add-on device 12' houses electronics 26 for detecting a selection of a drug dosage to be expelled and for recording the expelled drug dosage. The electronics 26 may comprise a processor 260, an interface circuitry 262, and a storage 264 for recorded data (FIG. 5). Details of the electronics 26 and its components and implemented functionality are described later particularly with reference to FIG. 5.

The add-on device 12', which is shown in FIG. 2 in a partial cross-sectional view, is attached to the injection pen 12 by clamping on the injection button 124 so that the injection button 124 can be turned and pushed by rotating and pushing the attached add-on device 12'. The add-on device 12' comprises a touch sensor 10 implemented as described in the following. An inner part 14 of the add-on device 12' is formed like a cap and is designed to be clamped on the injection button 123. Particularly, when attached to the injection button 124, the inner part 14 forms a rigid element. An outer part 16 of the add-on device 12' forms a touch element being coaxially arranged to the rigid element 14 such that a gap 18 is provided at least partly between the rigid element 14 and the touch element 16.

The touch element 16 is provided to enable a patient to select a drug dosage to be expelled and to expel the selected drug dosage. For the drug dosage selection, the patient may touch the touch element 16 and turn the add-on device 12' around the longitudinal axis of the body 120. The injection button 124 is rotated with the add-on device 12', which causes the dosage selecting mechanism to select a desired drug dosage to be expelled upon pressing the injection button 124. For expelling the selected drug dosage, the patient must push the add-on device 12' downwards in the direction of the longitudinal axis of the injection pen 12 such that the injection button 124 is also pushed to cause the (not shown) dosage selecting and expelling mechanism internally arranged in the body 120 to expel the selected drug dosage via the syringe 122.

As mentioned above, the touch element 16 is part of a touch sensor 10 of the add-on device 12', as well as the rigid element 14 of the add-on device 12'. The touch sensor 10 further comprises several pressure sensitive elements 22 circumferentially arranged in the gap 18 formed between the touch element 16 and the rigid element 14. The pressure sensitive elements 22 may comprise vibration elements, such as piezoelectric actuators, or electromechanical elements like vibration motors, and/or piezoelectric sensors.

The pressure sensitive elements 22 are positioned below a flexible part 20 of the touch element 16 in the gap 18, and may be fixed at the exterior side of the rigid element 14, the interior side of the touch element 16, or both. The pressure sensitive elements 22 may be particularly arranged in the gap to be clamped between the rigid element 14 and the touch element 16, while without any pressure on the touch element 14 the elements 22 do not produce an output signal for indicating a touch of the touch element 16, which means that any output signal of the elements 22 generated without pressure would not mean to indicate a touch. For example, a strain on the pressure sensitive elements 22 due to fabrication tolerances could incur the generation of any signal output of the pressure sensitive elements, but would not be deemed to be an output signal in the sense of the present disclosure.

The flexible part 20 may be for example formed by a thin wall of the touch element or a flexible material. The flexible part 20 is designed to be at least partly deformed upon exercising a pressure on it, particularly when a patient touches the touch element 16 and exercises a pressure 24 on the flexible part, which deforms the later at least partly, as shown in FIG. 2 by the dented part in dotted lines of the touch element 16. The at least partly deformation of the flexible part 20 reduces the gap 18 between the touch element 16 and the rigid element 14 at least in the area below the flexible part 20. This deformation of the flexible part 20 and particularly the reduction of the gap 18 may incur an at least partly transmission of the exercised pressure 24 to one or more of the pressure sensitive elements 22. Even if FIG. 2 shows the pressure 24 as being directed on the area of the flexible part 20 of the touch element 16, under which the pressure sensitive elements 22 are positioned, also a touch at different locations of the touch element 16 may be detectable, when this incurs a deformation of the flexible part 20 so that at least a part of the pressure 24 from the touch can be transmitted to the pressure sensitive elements 22.

Figure 3:
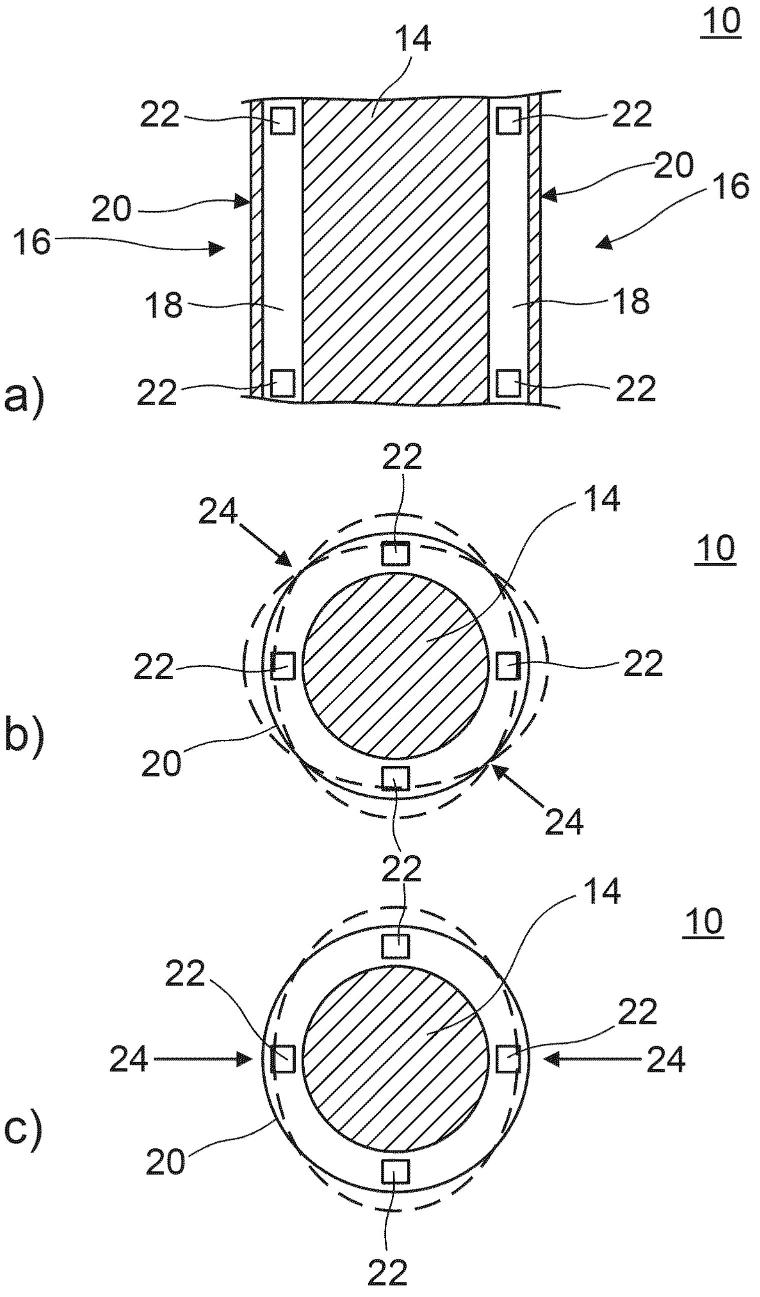
FIG. 3 shows examples of touch sensors with an arrangement of pressure sensitive elements and the principle of touch detecting with vibration and piezoelectric elements.

FIG. 3 *a*) shows an example of a touch sensor 10 with a specific arrangement of pressure sensitive elements in a cross-sectional side view: the rigid element 14 and the flexible sleeve shaped element 16 are arranged coaxially with a gap 18 between them, in which eight vibration elements used as pressure sensitive elements 22 are circumferentially arranged (two groups of four elements 22 in two different, parallel and in the longitudinal direction of the elements 14, 16 spaced planes, as shown in FIGS. 3 *b*) and 3 *c*)). The elements 22 may be vibration elements or piezoelectric elements. The touch detection principle underlying the different elements is explained now with regard to FIGS. 3 *b*) and 3 *c*):

FIG. 3 *b*) shows an example with vibration elements 22, for example piezoelectric actuators or electromechanical elements such as vibration motors excited to generate a defined vibration of the flexible element 16. The generated vibration may be a continuous or an impulse vibration with certain parameters such as duration, clocking of an impulse vibration and amplitude, and frequency of a continuous vibration being controllable via the excitation of the vibration elements 22, particularly by means of a vibration controller (not shown; the vibration controller may be for example implemented by the processor 260). The parameters can be selected to obtain a maximum sensitivity with regard to touching the flexible element 16. For example, the frequency and amplitude of a continuous vibration may be tuned to essentially match a resonance frequency of the entire touch sensor 10 and eventually also the drug delivery device comprising the touch sensor 10 or to which the touch sensor is attached.

In operation, the vibration elements 22 are excited to generate a vibration of the flexible element 16 with the desired parameters. The vibration is for example obtained by means of the above mentioned vibration controller, which may control the vibration elements 22 accordingly, particularly generate respective control signals (e.g. an electric voltage and current with an amplitude, frequency or clock, or duration) for the vibration elements 22. The vibration may be so weak that a user may hardly notice it, but strong enough to produce a technically detectable change of the vibration upon touching the flexible element 16. The touch of the flexible element 16 generates a pressure on the element 16 as indicated by the arrows 24. The pressure 24 influences the vibration of the elements 22, and particularly cause a damping of the vibration, which can be detected for example by the processor 260 (FIG. 5).

Figure 4:
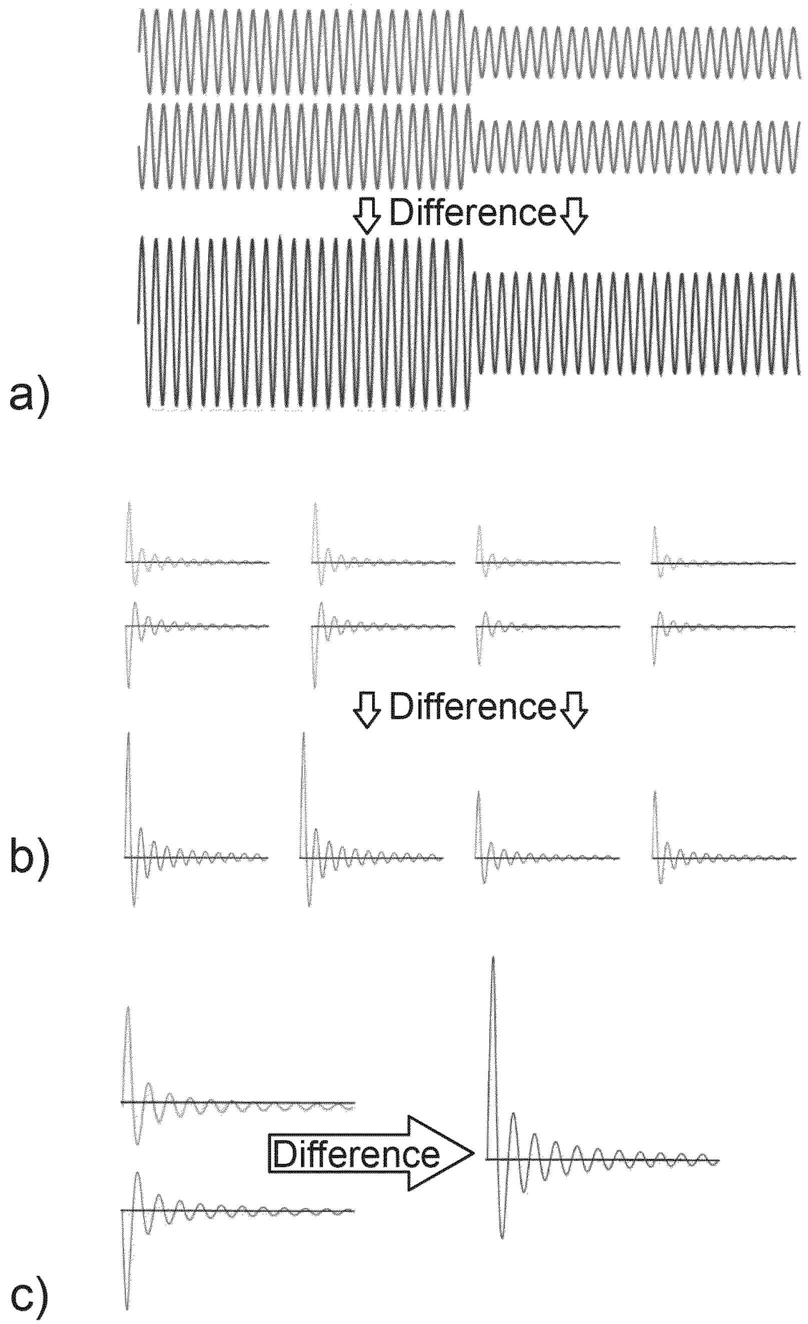
FIG. 4 shows exemplary courses of output signals of pressure sensitive elements of a touch sensor and courses of differential signals generated from the output signals

FIG. 4 *a*) shows an exemplary course of continuous vibration signals generated by two vibration elements 22 and the damping of the vibration signals when the flexible element 16 is touched. The pressure of the touch results in an immediate decrease of the amplitude of the continuous vibration signals. By generating a differential signal from the two single vibration signals as shown below in FIG. 4 *a*), the sensitivity of the detection of the touch can be further increased since the amplitude decrease caused by the touch may be amplified.

FIG. 4 *b*) shows an exemplary course of impulse vibration signals generated by two vibration elements 22 and the damping of the vibration signals when the flexible element 16 is touched. The pressure of the touch results in a faster decay of amplitude of the impulse vibration signals. By generating a differential signal from the two single vibration signals as shown below in FIG. 4*b*), the sensitivity of the detection of the touch can be further increased since the decay caused by the touch may be amplified.

FIG. 3 *c*) shows an example with piezoelectric sensors 22, for example piezoelectric ceramics or piezoelectric capacitors. When the flexible element 16 is touched by a user or patient to select a drug dosage to be expelled, the flexible element 16 is deformed, and the pressure 24 due to this deformation causes some sensors 22 to be compressed and others to be stretched. For example, the two sensors 22 to which the pressure arrows 24 point are compressed, while the other sensors 22 may be stretched by the deformation of the flexible element 16. Thus, the touch of the flexible element 16 results in the end in a deformation of not only the element 16, but also the sensors 22 coupled to the element 16 by being clamped in the gap 18 between the rigid element 14 and the flexible element 16. This deformation may cause electrical charges in the sensors in response to the pressures caused by compression and stretching. The electrical charges of the sensors 22 may be processed as output signals of the pressure sensitive elements implemented by the piezoelectric sensors 22.

FIG. 4 *c*) shows an exemplary course of two signals generated by two piezoelectric sensors 22 when the flexible element 16 is touched. The pressure of the touch results in impulses being indicative of the touch. By generating a differential signal from the two single sensor signals as shown below in FIG. 4*c*), the sensitivity of the detection of the touch can be further increased since the amplitudes of the spikes of the impulses caused by the touch may be amplified.

FIG. 5 shows a touch sensor 10 coupled to an electronics 26 for detecting and processing the output signals generated by the touch sensor 10, namely the pressure sensitive elements 22. The electronics 26 comprises a processor 260 for receiving and processing the output signals of the elements 22. The output signals may for example wake-up the electronics 26, particularly the processor 260 to execute a program for detecting a selection of drug dosage to be expelled with a drug delivery device such as an injection pen and to record an expelled drug dosage. The processor 260 may be also configured to generate one or more differential signals from the output signals in order to amplify the touch detection. The processor 260 may be coupled to a storage such as a ROM, RAM, PROM, Flash memory, which may be a program and/or data storage. For example the storage 264 may comprise a program comprising instructions for the processor 260 to process the output signals of the elements 22 of the touch sensor 10 such as initiating a drug dosage selecting and expelling detection.

The electronics 26 may also comprise a wired and/or wireless interface circuitry 262 enabling a communication with external devices. For example, the interface circuitry 262 may comprise one or more of the following: a wireless interface, particularly a Bluetooth®, Wi-Fi™, ZigBee™ a Near Field Communication interface; a wired interface, particularly a serial communication bus interface such as 12C, USB. The interface circuitry 262 may for example transmit a wake-up signal upon detecting a touch of the touch sensor 10 to an external device, for example a laptop, tablet computer or smartphone coupled with the interface circuitry 262 to receive and process data recorded by the electronics, or to the electronics of a drug injection device, particularly when the electronics 26 is comprised by an add-on device attached to the drug injection device (in this constellation, the add-on device comprising the electronics 26 may transmit upon touching the touch sensor 10 of the add-on device a wake-up signal to the electronics of the drug injection device to wake it up for dosage selection detection and recording.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N- tetradecanoyl)-des(B30) human insulin (insulin detemir, Levemir®); B29-N-palmitoyl-des(B30) human insulin;

B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A touch sensor, comprising:

a rigid element;

a touch element arranged in relation to the rigid element such that a gap between at least one part of the rigid element and a flexible part of the touch element is provided, wherein rotation of the touch element causes a drug dosage to be selected;

multiple pressure sensitive elements, at least one pressure sensitive element of the multiple pressure sensitive elements arranged in the gap between the at least one part of the rigid element and the flexible part of the touch element such that a pressure applied to the flexible part of the touch element deforms the flexible part to at least partly reduce the gap and at least partly transmit the applied pressure to the at least one pressure sensitive element, wherein the at least one pressure sensitive element is configured to generate an output signal upon detecting the pressure applied to the at least one pressure sensitive element, the generated output signal being provided for signaling that the flexible part of the touch element has been touched; and a processor configured to process the output signal of the at least one pressure sensitive element by detecting a change of a parameter of the output signal, wherein the processor is configured to generate a differential signal from two or more output signals of the multiple pressure sensitive elements as the output signal to be processed for detecting a change of the parameter.

2. The touch sensor of claim 1, wherein the rigid element comprises at least in part a cylindrical shape and the touch element is shaped as a sleeve coaxially arranged to surround the cylindrically shaped part of the rigid element.

3. The touch sensor of claim 1, wherein the touch sensor is included in a drug delivery device or a drug delivery add-on device.

4. The touch sensor of claim 3, wherein the rigid element and the touch element both form at least a part of a housing of the drug delivery device.

5. The touch sensor of claim 3, wherein the rigid element and the touch element both form at least a part of a housing of the drug delivery add-on device.

6. The touch sensor of claim 1, wherein the at least one pressure sensitive element comprises a vibration element configured to generate vibrations of the touch element and change the generated vibrations upon detecting a pressure applied to the at least one pressure sensitive element.

7. The touch sensor of claim 6, wherein the at least one pressure sensitive element comprises one of a piezoelectric actuator or an electromechanical element.

8. The touch sensor of claim 7, wherein the at least one pressure sensitive element comprises a vibration motor.

9. The touch sensor of claim 6, comprising a vibration controller configured to control the vibration element to generate continuous vibrations and/or impulse vibrations of the touch element and generate the output signal depending on detecting a changing of the generated vibrations.

10. The touch sensor of claim 9, wherein the vibration controller is configured to control sensitivity and/or power demand of the at least one pressure sensitive element by setting duration and/or pulsing of the impulse vibrations, and/or an amplitude and/or a frequency of the continuous vibrations.

11. The touch sensor of claim 10, wherein the vibration controller is configured to set the frequency of the continuous vibrations in a range comprising a resonance frequency of a drug delivery device or a drug delivery add-on device.

12. The touch sensor of claim 1, wherein the at least one pressure sensitive element comprises a piezoelectric sensor.

13. The touch sensor of claim 1, wherein the processor is configured to output a touch detection signal upon detecting a change of amplitude and/or frequency of the output signal.

14. The touch sensor of claim 1, comprising an interface for transmitting the output signal, wherein the interface comprises one or more of the following: a wireless interface including a Bluetooth®, Wi-Fi™, or ZigBee™, a Near Field Communication interface; or a wired interface, wherein the wired interface comprises a serial communication bus interface including an I2C interface or a USB interface.

15. A drug delivery device comprising a touch sensor, wherein the touch sensor comprises:

a rigid element;

a touch element arranged in relation to the rigid element such that a gap between at least one part of the rigid element and a flexible part of the touch element is provided, wherein rotation of the touch element causes a drug dosage to be selected;

multiple pressure sensitive elements, at least one pressure sensitive element of the multiple pressure sensitive elements arranged in the gap between the at least one part of the rigid element and the flexible part of the touch element such that a pressure applied to the flexible part of the touch element deforms the flexible part to at least partly reduce the gap and at least partly transmit the applied pressure to the at least one pressure sensitive element, wherein the at least one pressure sensitive element is configured to generate an output signal upon detecting the pressure applied to the at least one pressure sensitive element, the generated output signal being provided for signaling that the flexible part of the touch element has been touched; and a processor configured to process the output signal of the at least one pressure sensitive element by detecting a change of a parameter of the output signal, wherein the processor is configured to generate a differential signal from two or more output signals of the multiple pressure sensitive elements as the output signal to be processed for detecting a change of the parameter.

16. The drug delivery device of claim 15, comprising an electronics configured for one of the following: processing an output signal generated by the at least one pressure sensitive element for determining a user input; transmitting an output signal generated by the at least one pressure sensitive element for determining a user input via an interface; or storing a user input determined by processing an output signal generated by the at least one pressure sensitive element.

17. A drug delivery add-on device comprising a touch sensor, wherein the touch sensor comprises:

a rigid element;

a touch element arranged in relation to the rigid element such that a gap between at least one part of the rigid element and a flexible part of the touch element is provided, wherein rotation of the touch element causes a drug dosage to be selected;

multiple pressure sensitive elements, at least one pressure sensitive element of the multiple pressure sensitive elements arranged in the gap between the at least one part of the rigid element and the flexible part of the touch element such that a pressure applied to the flexible part of the touch element deforms the flexible part to at least partly reduce the gap and at least partly transmit the applied pressure to the at least one pressure sensitive element, wherein the at least one pressure sensitive element is configured to generate an output signal upon detecting the pressure applied to the at least one pressure sensitive element, the generated output signal being provided for signaling that the flexible part of the touch element has been touched; and a processor configured to process the output signal of the at least one pressure sensitive element by detecting a change of a parameter of the output signal, wherein the processor is configured to generate a differential signal from two or more output signals of the multiple pressure sensitive elements as the output signal to be processed for detecting a change of the parameter.

18. The drug delivery add-on device of claim 17, comprising an electronics configured for one of the following: processing an output signal generated by the at least one pressure sensitive element for determining a user input; transmitting an output signal generated by the at least one pressure sensitive element for determining a user input via an interface; or storing a user input determined by processing an output signal generated by the at least one pressure sensitive element.

* * * * *